United States Patent [19]
Dennis

[11] Patent Number: 6,093,176
[45] Date of Patent: Jul. 25, 2000

[54] TROCAR WITH DISPOSABLE VALVE AND REUSABLE CANNULA

[75] Inventor: William G. Dennis, Jacksonville, Fla.

[73] Assignee: Core Dynamics, Inc., Jacksonville, Fla.

[21] Appl. No.: 09/037,209

[22] Filed: Mar. 10, 1998

[51] Int. Cl.[7] .................................................. A61M 5/00
[52] U.S. Cl. ........................ 604/256; 604/164; 604/167; 604/246; 604/278
[58] Field of Search .............................. 604/48, 264, 272, 604/275, 278, 158, 161, 164, 166, 167, 169, 170, 256

[56] References Cited

U.S. PATENT DOCUMENTS

| | | | |
|---|---|---|---|
| 4,626,245 | 12/1986 | Weinstein | 604/167 |
| 4,655,752 | 4/1987 | Honkanen et al. | 604/256 |
| 5,009,391 | 4/1991 | Steigerwald | 251/149.1 |
| 5,059,186 | 10/1991 | Yamamoto et al. | 604/280 |
| 5,092,857 | 3/1992 | Fleischhacker | 604/256 |
| 5,385,552 | 1/1995 | Haber et al. | 604/167 |
| 5,584,850 | 12/1996 | Hart et al. | 604/185 |
| 5,603,702 | 2/1997 | Smith et al. | 604/256 |
| 5,634,908 | 6/1997 | Loomas | 604/167 |
| 5,871,471 | 2/1999 | Ryan et al. | 604/167 |
| 5,895,377 | 4/1999 | Smith et al. | 604/167 |
| 5,980,493 | 11/1999 | Smith et al. | 604/164 |
| 5,989,224 | 11/1999 | Exline et al. | 604/167 |

*Primary Examiner*—Mark O. Polutta
*Assistant Examiner*—Patricia Bianco
*Attorney, Agent, or Firm*—McGuire, Woods, Battle & Boothe, LLP

[57] ABSTRACT

A modular trocar assembly having a cannula, a passive valve seal assembly and an instrument seal assembly all releasably joined to define a central axial bore, where the passive valve seal assembly contains a valve seal which prevents passage of gas through the trocar assembly into the atmosphere when no instrument is inserted but which opens to allow for insertion of an instrument, and where the instrument seal assembly contains an instrument reducer seal which prevents passage of gas through the trocar assembly into the atmosphere when an instrument is inserted through the valve seal. The passive valve seal assembly and the instrument seal assembly are preferably composed of plastic so as to be disposable, while the cannula is preferably composed of a sterilizable material to enable reuse.

13 Claims, 5 Drawing Sheets

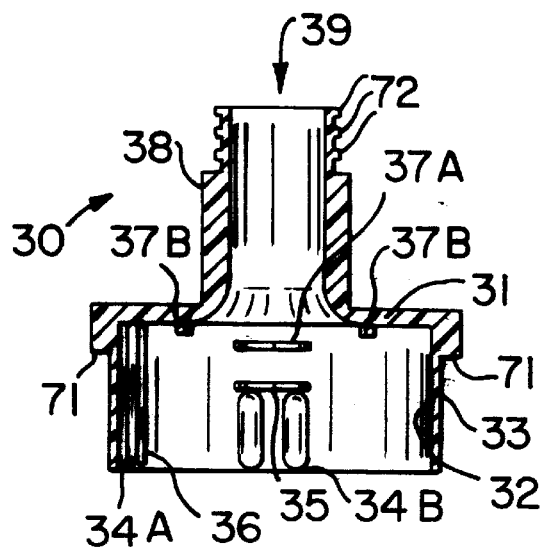
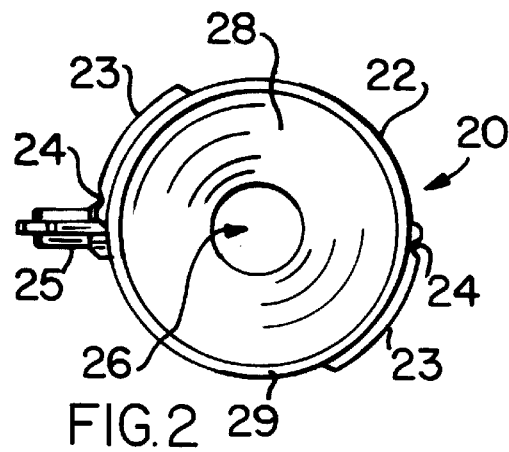
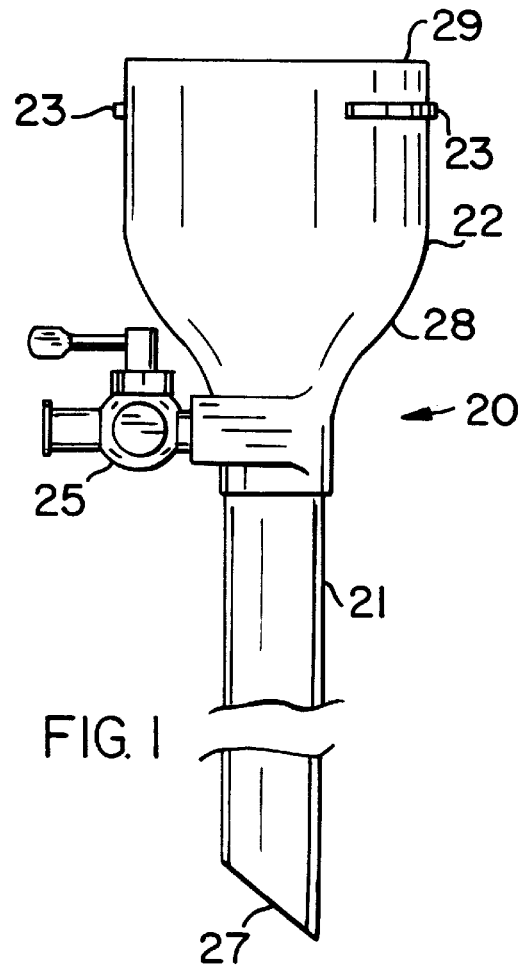

TROCAR WITH DISPOSABLE VALVE AND REUSABLE CANNULA

BACKGROUND OF THE INVENTION

This invention relates generally to the field of surgical trocar systems which provide a sealed passageway for insertion and removal of various instruments through a hole in the body wall to reach an internal cavity, where a hollow, tubular cannula maintains an open channel and one or more valves define a seal to close the open channel when no instrument is inserted as well as to seal around an inserted instrument. More particularly, the invention relates to such devices where the trocar assembly is formed of detachable component members, such that the valves are disposable yet the cannula may be sterilized and reused.

Trocar systems are well known in the surgical field. In many procedures, such as laporascopic surgery, access to an internal cavity is achieved by puncturing a relatively small hole through the body wall using a pointed trocar in combination with a tubular cannula, or a sharpened cannula/trocar in combination with an internal obturator. The pointed trocar or obturator is removed from the hollow cannula to open the passageway and typically the internal cavity is distended by introducing a gas into the cavity. A valve seal made of an elastomeric material is used to seal the cannula to prevent escape of the gas from the cavity. Slits or other aperture means in the seal allow an instrument to be inserted through the valve to perform an operation in the internal cavity. Since the instrument must be smaller in outer diameter than the inner diameter of the cannula to allow for insertion and relative movement within the cannula, the seal, or an additional seal, is designed to also prevent gas from escaping through the cannula past the instrument. There are numerous examples of such trocar systems in the art, as well as numerous constructions for the valve seals.

SUMMARY OF THE INVENTION

The trocar system of the invention is a multiple component or modular apparatus having at least two detachable or interchangeable main component members or assemblies, one of which consists in general of a cannula, and the other of which consists in general of a passive valve seal assembly and an active instrument or reducer seal assembly. The trocar system provides a gas-tight seal to prevent passage of gas through the system, with the passive valve seal member comprising means to seal the cannula passageway when no instrument is inserted into the trocar system and the instrument reducer seal member comprising means to seal the passageway in conjunction with an instrument inserted into the cannula.

The cannula comprises an elongated, hollow tube which defines a passageway or axial bore for an instrument and has an open distal end and an expanded mating member on the proximal end, circular in cross-section, for joining the cannula to the valve seal assembly. A pair of opposing cannula detent flanges, each extending approximately 75 degrees around the circumference, are positioned on the exterior of the mating member a short distance from the distal end opening. Each of the cannula flanges is preferably provided with a detent groove or catch member adjacent one end.

The valve seal assembly comprises a housing, generally circular in cross-section and defining and axial bore, having open distal and proximal ends, where the distal end is sized to mate externally with the cannula mating member. The valve seal housing at the proximal end is significantly smaller in diameter than at the distal end, with the two ends joined by a shoulder generally perpendicular to the longitudinal axis. The proximal end mates with the instrument seal assembly and is generally tubular in configuration. The interior wall of the cannula mating portion is generally annular except for the presence of a number of inwardly extending alignment members, oriented in parallel manner in the axial direction, which comprise two opposing pairs of ribs which define the axial pathway for insertion of the cannula mating member into the valve seal housing, the pathway ribs within each set being spaced slightly farther than 65 degrees, the circumferential distance of the cannula ribs, such that the cannula can be inserted in the axial direction into the valve seal assembly with each of the cannula ribs fitting between a pair of the pathway ribs. The interior diameter defined by the innermost surfaces of the pathway ribs is only slightly larger than the exterior diameter of the mating member to create a relatively snug fit between the two components. In each set of pathway ribs, one rib is longer than the other, with one rib extending preferably to the shoulder and extending inwardly from the internal wall sufficient distance to provide a rotation stop against which the cannula ribs abut and cannot pass. The shorter rib extends only about halfway into the valve seal assembly and is capped with a circumferentially extending detent flange. With the cannula inserted within the valve assembly, the pieces can be rotated up to about 90 degrees such that the circumferential cannula ribs pass to the proximal side of the two opposing detent flanges, which prevents axial separation of the two members. Adjacent each of the long ribs defining the insertion pathway is a detent rib or member which extends a shorter distance from the internal wall than the pathway ribs, such that the cannula ribs can be forced past the detent ribs to a point where the detent ribs seat in the detent grooves on the cannula ribs to lock the two members rotationally. Rotation past the detent ribs is stopped by the rotation stop pathway ribs.

The valve seal assembly further comprises seal retention flange members to retain the elastomeric seal within the assembly. A pair of circumferentially extending flange members mounted on the internal wall of the valve seal assembly prevent axial movement of the seal within the assembly, and a pair of curved flange members mounted on the interior of the shoulder prevent radial movement of the seal. The valve seal itself is of the type known as a duckbill seal, having an annular seating member defining a large circular opening, with the seating member having an annular receiving channel on its distal side. A circular wall extends distally from the seating member and transitions into two planar valve members which join along a line intersecting the longitudinal axis and extending across the entire circular wall, where the line contains a slit such that an instrument can be inserted through the valve seal. The valve seal remains closed in the passive state, i.e., where no instrument is inserted to separate the slit and planar valve members. To account for the long pathway ribs and the detent ribs, the annular seating member is provided with two sets of opposing rib slots corresponding in configuration and positioning to the configuration and positioning of the ribs. When the seal is inserted into the passive valve seal assembly, annular seating member abuts the interior of the shoulder and the two pairs of seal retention flanges. When the cannula is inserted into the valve seal assembly, the proximal end of the mating member seats in the annular receiving channel of the seal.

The active instrument or reducer seal assembly mounts onto the proximal end of the valve seal assembly, either in a permanent or releasable manner, or the combination of valve seal assembly and instrument seal assembly is initially formed as an integral member, and comprises a distal mating portion sized to receive the proximal end of the valve seal assembly, a transition shoulder to increase the outer diameter of the instrument seal assembly, an annular wall portion and an end wall perpendicular to the longitudinal axis which has a relatively large circular opening, all operating to define an axial bore. Mounted within the instrument seal assembly is an elastomeric seal having a generally small central aperture, such that the seal forms a gas-tight seal against an instrument when the instrument is inserted through the central aperture. Thus when no instrument is present, the duck bill valve seal prevents gas from passing through the device, but when an instrument is inserted, thereby opening the passive valve seal, the active instrument seal prevents passage of gas by tightly surrounding the instrument. Because the invention is modular, the combined valve seal assembly and instrument seal assembly, or either the valve seal assembly or instrument seal assembly alone if both are detachable, may be discarded and replaced as necessary while the cannula portion can be sterilized and reused.

BRIEF DESCRIPTION OF THE DRAWINGS

FIG. 1 is a side view of the cannula portion of the trocar system.

FIG. 2 is an axial view of the proximal end of the cannula portion.

FIG. 6 is a cross-sectional view of the valve seal assembly taken along line 6—6 of FIG. 4, showing certain elements as exposed.

DETAILED DESCRIPTION OF THE INVENTION

With reference to the drawings, the invention will now be described in detail with regard for the best mode and the preferred embodiment. As used herein, the term proximal shall refer to the direction or side of a component member which is external to the body when the device is in use, i.e., the non-puncturing side, and the term distal shall refer to the direction or side of a component member which is internal to the body when the device is in use, i.e., the puncturing side.

Figure 18:
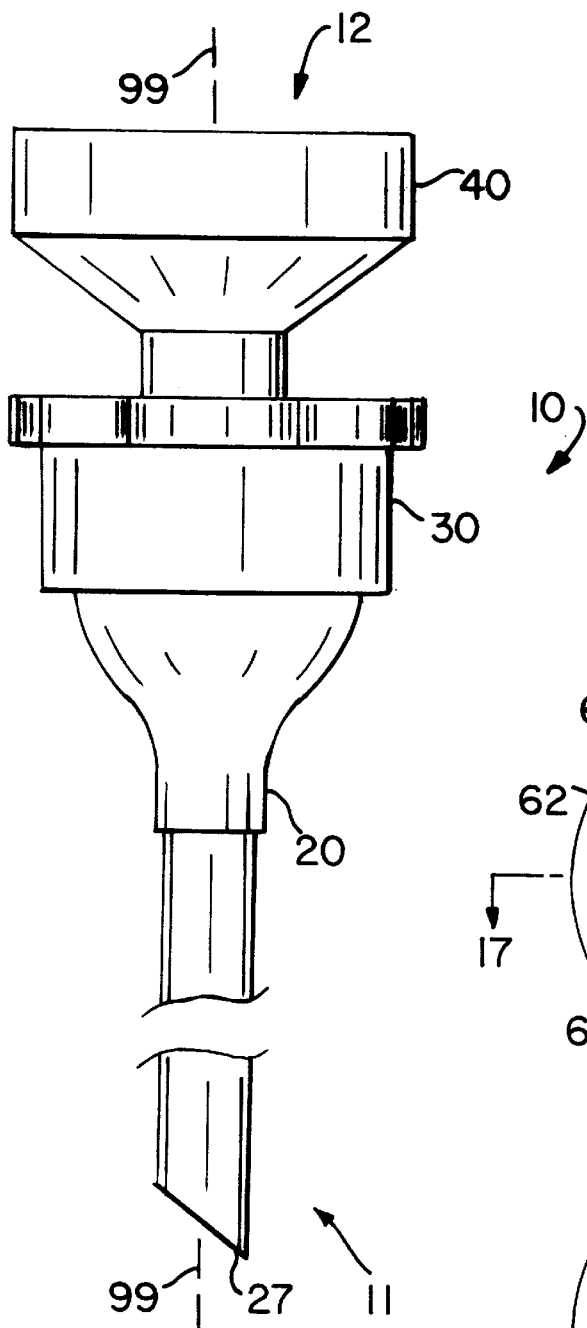
FIG. 18 is a side view of the assembled trocar system.
Figure 15:
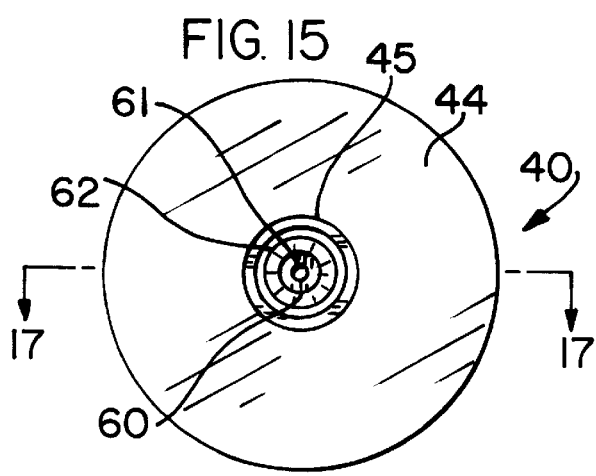
FIG. 15 is an axial view of the proximal end of the instrument seal assembly.
Figure 16:
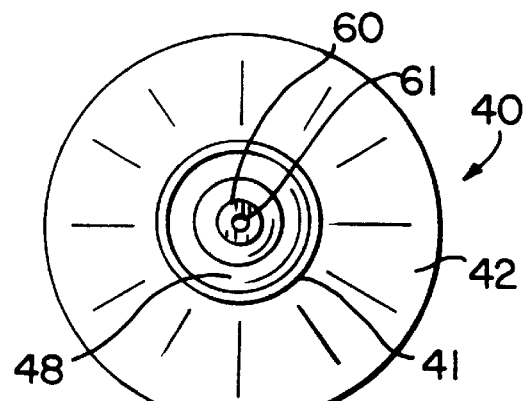
FIG. 16 is an axial view of the distal end of the instrument seal assembly.

As shown in FIG. 18, the invention is a trocar system or apparatus 10 generally comprising a cannula 20, a passive valve seal assembly 30 and an active instrument or reducer seal assembly 40, all joined coaxially along longitudinal axis 99, with the cannula 20 positioned on the distal end 11 and the instrument seal assembly 40 positioned on the proximal end. It would also be possible to exchange the relative position of the passive valve assembly 30 and the instrument seal assembly 40 so that the passive valve assembly 30 is at the proximal end 12, provided suitable changes are made in the mating mechanisms. It is also possible to form the passive valve seal assembly 30 and the active instrument seal assembly 40 as a single member releasably joined to the cannula 20. The tip 27 of the cannula 20 can be bevelled and sharpened, such that the cannula tip 27 in combination with an obturator (not shown) is the piercing means for inserting the cannula 20 through the body wall of the patient. Alternatively, the cannula tip 27 can be blunt and used in combination with a pointed trocar member (also not shown), which is the other common design for a trocar system 10. Both such combinations are well known in the art.

Referring now to FIGS. 1 and 2, the cannula 20 is seen to comprise a hollow tubular member generally extended in the longitudinal direction, and is preferably constructed of a metal which is very durable, relatively easy to machine, and which can be sterilized for reuse, such as surgical grade stainless steel or the like. The distal portion of the cannula 20 comprises a hollow tube 21, relatively thin-walled and preferably circular in cross-section, with an open tip 27 at the most distal end. The proximal end of the cannula 20 is open and comprises a mating member 22 and rim 29, also relatively thin-walled and circular in cross-section, which has a much larger diameter than that of tube 21. The mating member 22 is joined to the tube 21 by a transition shoulder or flared portion 28, the combination of all three members 21, 28 and 22 defining an internal axial bore 26 completely therethrough which allows passage of gases and instruments through the cannula 20. The cannula 20 is shown with a stopcock valve 25 extending radially from tube 21, mounted to the cannula 20 with a threaded coupling, which communicates with the axial bore 26 for the introduction or removal of gases into the body cavity. Other valve mechanisms or means to introduce the gas into the cannula 20 which are equivalent to stopcock valve 25 are known in the art and could be substituted therefore. Overall size and dimensions of the cannula 20 will vary with intended use and other requirements, but dimensions for a representative example can be an overall length of about 6 inches, with tube 21 comprising about 5 inches and mating member 23 about 0.600 inches of the overall length, an external diameter for tube 21 of about 0.630 inches with an internal diameter of about 0.507 inches, and an external diameter for mating member 22 of about 1.030 inches and an internal diameter of about 0.980 inches.

Positioned on the exterior of the mating member 22 about 0.250 inches from the open rim 29 are cannula detent flanges 23, preferably comprising two opposing flanges 23 mounted 180 degrees apart. The cannula detent flanges 23 extend circumferentially about mating member 22, preferably parallel to the rim 29 or in a slightly helical or slanted manner so as to form a cam surface when the cannula 20 is rotated relative to the passive valve seal assembly 30. The cannula flanges 23 are relatively short in the axial and radial direction, extending about 0.050 inches outward and the same longitudinally. Each of the cannula flanges 23 extends preferably about 75 degrees about the circumference of the mating member 22, leaving an unobstructed arc of about 105 degrees between each cannula detent flange 23, and may be formed with bevelled or rounded ends. A small, external detent groove or indention 24 is positioned adjacent one end of each cannula flange 23, preferably about 10 degrees from the end of each flange 23 and spaced approximately 180 degrees apart from each other, and each is designed to receive a detent rib member 36 on the internal wall 32 of the passive valve seal assembly 30 to provide a rotational mechanical or frictional interlock means between the cannula 20 and the passive valve seal assembly 30. The radial height of the portion of the cannula flange 23 between the detent groove 24 and its adjacent end may be shortened approximately 0.006 inches to reduce stress when the cannula 20 and passive valve seal assembly 30 are rotated in a relative manner to lock or unlock the two components 20 and 30.

In the embodiment where the passive valve seal assembly 30 and the instrument seal assembly 40 are detachable from each other, the middle component of the trocar apparatus 10 is preferably the passive valve seal assembly 30 and is shown in FIGS. 3 through 8. The passive valve seal assembly 30 comprises generally a relatively thin-walled and circular in cross-section cannula mating portion or member 33 on the distal side, a reduction shoulder 31 and a relatively thin-walled and circular in cross-section instrument seal assembly mating portion or member 38 on the proximal side, with all three components preferably formed as a unitary molded plastic piece and defining an internal axial bore 39 which passes completely therethrough. Since the passive valve seal assembly 30 is releasably joined to the cannula 20, certain dimensions must correspond to the dimensions of the cannula 20 to enable mating. For the representative cannula 20 dimensions set forth above, the passive valve seal assembly 30 is preferably approximately 1.285 inches in length, with the cannula mating portion 33 comprising about 0.675 inches and the instrument seal assembly mating portion 38 comprising about 0.610 inches of the overall length. The outer diameter of the cannula mating portion 33 is about 1.265 inches and the outer diameter of the instrument seal assembly mating portion 38 is about 0.750 inches except at the proximal end where the outer diameter is reduced to about 0.650 and a number of circumferential interlock flanges 72 are provided as part of seal assemblies mating means to create a secure but releasable connection between the passive valve seal assembly 30 and the instrument seal assembly 40. The reduction shoulder 31 is preferably formed perpendicular to the longitudinal axis 99 and further comprises gripping means such as rotation tabs 71 to enable the user to better grasp the passive valve seal assembly 30, with the tabs 71 each extending radially outward about 0.125 inches from the exterior of the cannula mating portion 33. The internal diameter of the instrument seal assembly mating portion is about 0.510 inches and the interior diameter of the internal annular wall 32 of the cannula mating portion 33 is approximately 1.145 inches, with the internal length of the cannula mating portion 33 extending about 0.625 inches to the distal side of the reduction shoulder 31.

Figure 3:
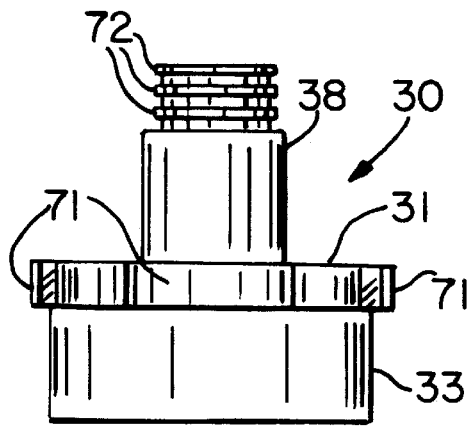
FIG. 3 is a side view of the valve seal assembly portion of the trocar system.
Figure 4:
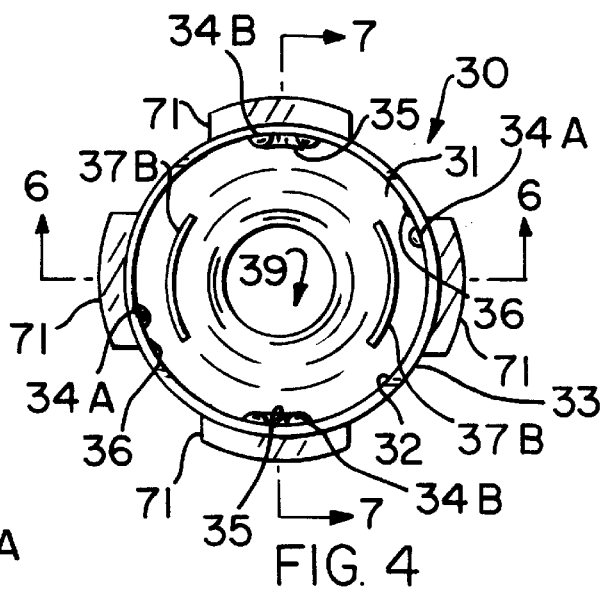
FIG. 4 is an axial view of the distal end of the valve seal assembly, with the valve seal removed.
Figure 7:
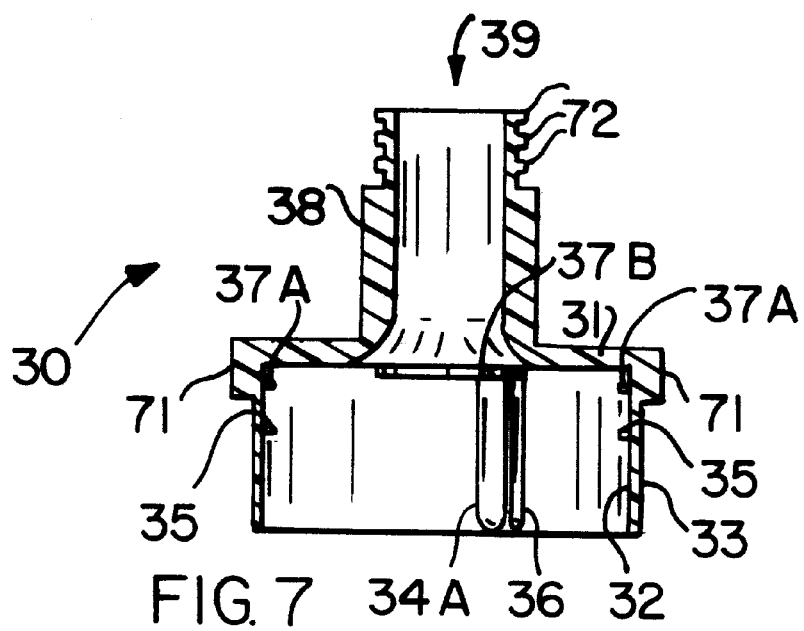
FIG. 7 is a cross-sectional view of the valve seal assembly taken along line 7—7 of FIG. 4, showing certain elements as exposed.
Figure 14:
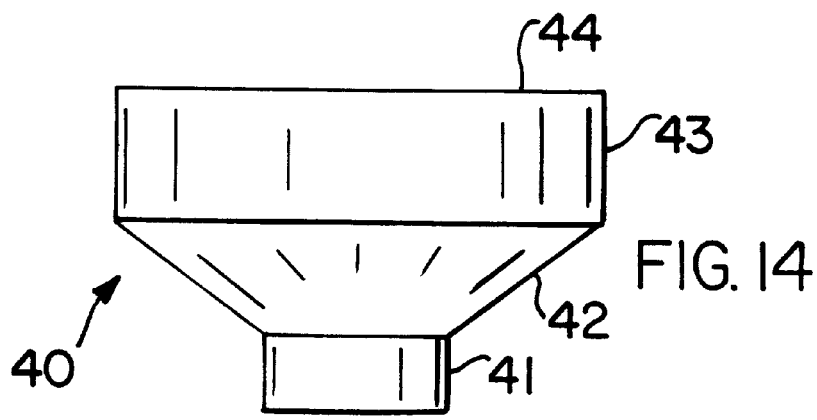
FIG. 14 is a side view of the instrument seal assembly.
Figure 17:
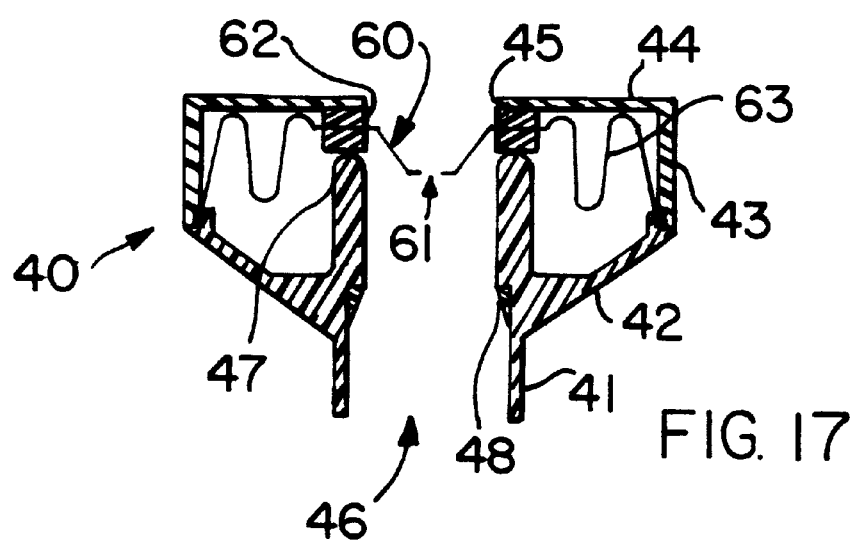
FIG. 17 is a cross-sectional view of the instrument seal assembly taken along line 17—17 of FIG. 15.
Figure 9:
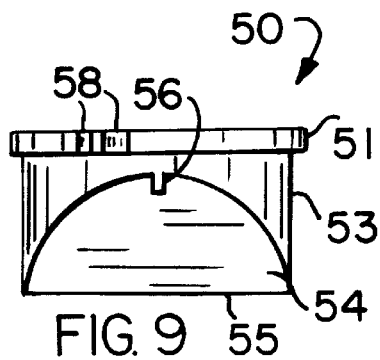
FIG. 9 is a side view of the valve seal, as seen perpendicular to the valve slit.
Figure 10:
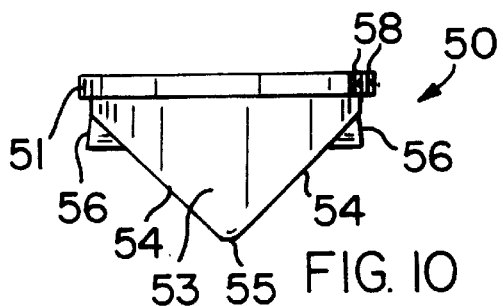
FIG. 10 is side view of the valve seal, as seen parallel to the valve slit, which is a 90 degree rotation from FIG. 9.
Figure 11:
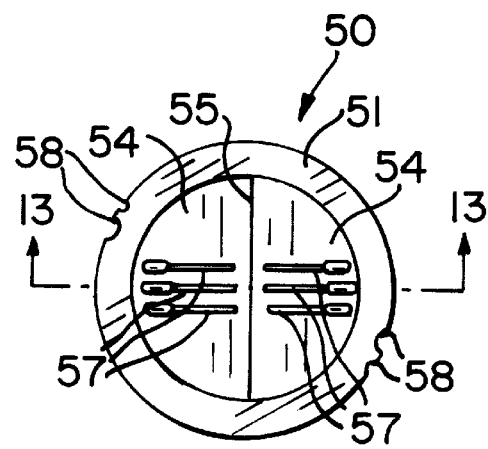
FIG. 11 is an axial view of the distal end of the valve seal.
Figure 13:
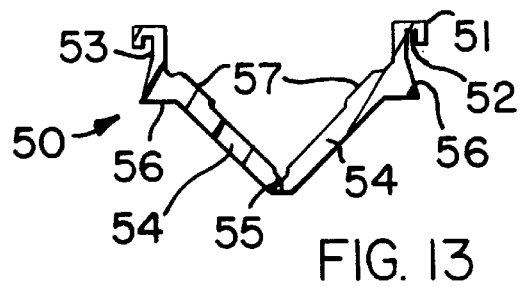
FIG. 13 is a cross-sectional view of the valve seal taken along line 13—13 of FIG. 11.
Figure 12:
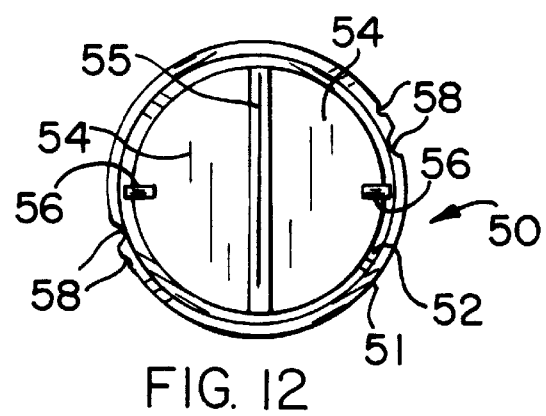
FIG. 12 is an axial view of the proximal end of the valve seal.

As shown best in FIGS. 4, 6 and 7, abutting the interior side of the cannula mating portion 33 and the distal side of the reduction shoulder 31 are various means to align and join the cannula 20 to the passive valve seal assembly 30, as well as means to retain the passive valve seal member 50 in the passive valve seal assembly 30. The alignment means comprise two pairs of pathway ribs 34, generally semi-circular or curved in lateral cross-section, with each pair comprising a rotation stop rib 34a and a short pathway rib 34b, all of ribs 34 being generally axially oriented and parallel. The pathway ribs 34 are mounted on the internal wall 32 such that within each pair the rotation stop rib 34a is separated from the short pathway rib 34b a distance slightly greater than 75 degrees, the circumferential arc of each of the cannula detent flanges 23 on the exterior of the mating member 22 of the cannula 20. The two rotation stop ribs 34a are positioned 180 degrees apart, as are the two short pathway ribs 34b. The rotation stop ribs 34a preferably extend from the distal end of the cannula mating portion 33 to the distal side of the reduction shoulder 31. The short pathway ribs 34b extend partially along the internal wall 32 about 0.270 inches from the open distal end and are adjoined to or transition into one of a pair of axial detent flanges or lifters 35, each of which extend circumferentially around the internal wall 32 a distance of about 20 degrees and extend inwardly about 0.055 inches. Each pair of pathway ribs 34 define an axial pathway into which the cannula detent flanges 23 of the cannula mating member 22 may be inserted. At full insertion, the cannula 20 and/or the passive valve seal assembly 30 are relatively rotated such that the cannula detent flanges 23 pass onto the proximal side of the axial detent flanges 35, which prevent separation in the axial direction of the cannula 20 and passive valve seal assembly 30. Preferably, the leading edges of the axial detent flanges 35 are bevelled or curved so that the cannula mating member 33 is pressed into the passive valve seal assembly 30 in a cam-like manner as rotation occurs. As the relative amount of rotation approaches 90 degrees, the leading end of each cannula detent flange 23 passes over a detent rib 36. Each detent rib 36 preferably extends the full interior axial length of the cannula mating portion 33. The detent ribs 36 are also curved or semi-circular in cross-section, but are smaller in dimension than the rotation stop pathway ribs 34a. Force must be exerted to rotate the cannula detent flanges 23 past the detent ribs 36, and the rotation is limited when the leading end of each cannula detent flange 23 meets the rotation stop pathway rib 34a, at which point the detent rib 36 seats in the detent groove 24 in each cannula detent flange 23, preventing accidental reverse rotation. To separate the cannula 20 and the passive valve seal assembly 30, rotational force sufficient to release the detent ribs 36 from the detent grooves 24 is applied. When the relative rotation is approximately 90 degrees, the end of each cannula detent flange 23 strikes the opposing rotation stop rib 34a, aligning the cannula detent flanges 23 between each pair of pathway ribs 34 so that the cannula 20 and passive valve seal assembly can be separated in the axial direction.

Figure 8:
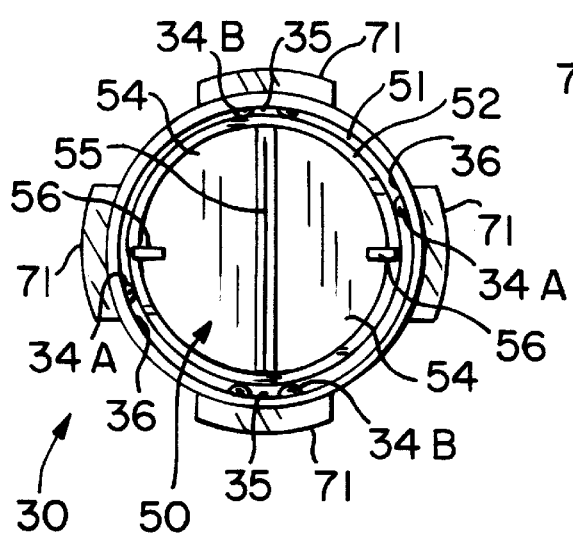
FIG. 8 is an axial view of the distal end of the valve seal assembly with the valve seal in place.
Figure 5:
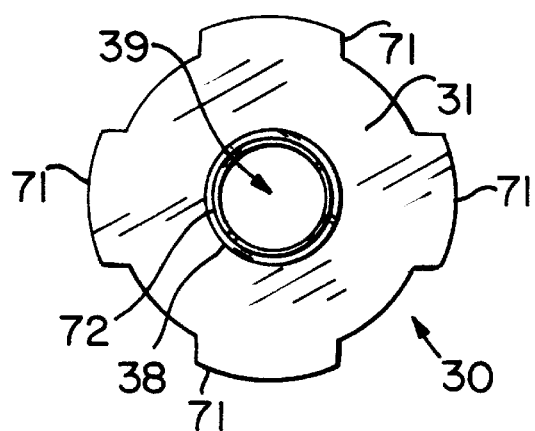
FIG. 5 is an axial view of the proximal end of the valve seal assembly.

The passive valve seal assembly 30 further comprises a passive valve seal 50, which is preferably of the duck-bill type as shown in FIGS. 8 through 13. The valve seal 50 is made of an elastomeric or plastic material and comprises an annular seating member 51 containing an annular receiving channel 52 on its distal side, a circular wall 53 extending in the distal direction truncated by a pair of planar valve members 54 which meet linearly at the distal end of the valve seal 50 at a slit 55 which passes through the longitudinal axis and extends across to both sides of the circular wall 53. The slit 55 is closed in the passive state and thus prevents passage of gases through the valve seal 50, but can be separated by forcing an instrument through the valve seal 50. The planar valve members 54 may further be provided with a number of reinforcing ribs 57 to increase resistance to tearing when sharp instruments are inserted as well as to help maintain the planar configuration of the valve members 54. A pair of opposing brace members 56, designed to abut against the interior wall of the cannula mating member 22, may also be provided to assist in maintaining closure of the valve seal 50 in the passive state. The dimensions of the valve seal 50 must correspond to the dimensions of the cannula mating member 33 and the passive valve seal assembly 30, and in relation to the dimensions given above may have an external diameter for the annular seating member of about 1.145 inches, an outer diameter for the circular wall 53 of about 0.965 inches and an axial length of about 0.600 inches, with the annular seating member 51 extending about 0.090 inches in the axial direction and the receiving channel 52 extending about 0.045 inches into the distal side of the annular seating member 51. Positioned around the perimeter of the annular seating member 51 are two pairs of 180 degree opposing rib slots 58, sixed and configured to correspond to the rotation stop pathway ribs 34a and the detent ribs 36, such that when the valve seal 50 is inserted axially into the cannula mating portion 33, as seen in FIG. 8, the valve seal 50 is prevented from rotating. Additional means to secure and retain the valve seal 50 properly seated within the passive valve seal assembly 30 comprise seal retention flange members 37. Seal retention flange members 37 are shown to comprise a pair of axial seal stop members 37a mounted onto internal wall 32 of the cannula mating portion 33 about 0.100 inches from the distal side of the reduction shoulder 31. These axial stops 37a extend a short distance circumferentially and, once the annular seating member 51 of the valve seal 50 has been pressed into the cannula mating portion 33, abut the distal side of the annular seating member 51 to prevent movement in the axial direction. A second pair of seal retention flange members 37, radial seal stop flanges 37b, are mounted on the distal side of the reduction shoulder 31. The radial stop flanges 37b are curved and extend about 0.500 inches, and are positioned about 0.845 inches apart to fit into and abut the interior side of the annular seating member 51, thereby preventing the annular seating member 51 from collapsing inwardly when an instrument is inserted.

With the valve seal 50 seated within the passive valve seal assembly 30, the rim 29 of the mating member 33 of the annular 20 fits into the receiving channel 52 on the seating member 51. the thickness of the seating member 51 is such that the elastomeric material must be forcibly compressed in the axial direction to allow relative rotation of the cannula 20 and passive valve seal assembly 30 to cause the cannula detent flanges 23 to pass over the axial detent flanges 35 on the internal wall 32 of the cannula mating portion 33. This compression insures a gas-tight seal between the rim 29 of the cannula mating member 33 and the receiving channel 52 as well as between the proximal side of the annular seating member 51 and the distal side of the reduction shoulder 31. The compression also assists in securing the cannula 20 to the passive valve seal assembly 30 to prevent accidental rotation.

The third or most proximal component of the trocar apparatus 10 is the instrument seal assembly 40, as shown in FIGS. 14 through 17. The instrument seal assembly 40 comprises in general a valve seal assembly mating portion 41 on the distal end, an expansion shoulder 42 joining the mating portion 41 to an annular wall 43 and an end or cap wall 44 which has a circular opening 45, the components preferably formed of a plastic material, with the combination defining an axial bore 46. The dimensions are such that the instrument seal assembly 40 releasably mates with the passive valve seal assembly 30, the mating portion 41 receiving the instrument seal assembly mating portion 38 of the passive valve seal assembly 30. A ring seal 48 is mounted within the axial bore 46 at a point of internal diameter reduction so that the interlock flanges 72 compress the ring seal to frictionally secure the two components 30 and 40 together. An instrument seal 60 formed of an elastomeric material and having a relatively small, central, circular aperture 61 is positioned in the axial bore 46. The central aperture 61 is sized so as to be slightly smaller than the diameter of any instruments to be inserted into the trocar 10, so that the instrument seal 60 is stretched tightly about the instrument to prevent passage of gas. The instrument seal 60 may be of the type known as a bellows or accordion seal, such that the instrument seal 60 has a number of pleated portions 63 which allow the central aperture 61 of the seal 60 to shift off the longitudinal axis 99 when an instrument is inserted or moved, thereby insuring that the seal formed around the instrument by the central aperture 61 remains gas-tight. A sliding collar 62 abutting the distal side of the end wall 44 and supported by collar support 47 on its distal side may be utilized to reduce axial movement of the seal 60 during instrument insertion and removal. The instrument seal assembly 40 and the valve seal assembly 30 may also be assembled within a single housing or permanently joined.

The trocar assembly 10 is assembled for use connecting the cannula 20, passive valve seal assembly 30 and instrument seal assembly as shown in FIG. 18. In this manner axial bores 26, 39 and 46 are coaxially aligned along the longitudinal axis 99 to create an open common axial bore through the entire trocar assembly 10. With no instrument inserted, the passive valve seal 50 in the passive valve seal assembly 30 remains in the closed position, thus preventing any gas from passing through the passive valve seal assembly 30 and into the atmosphere. When an instrument is inserted, the body of the instrument passes through the central aperture 61 of the instrument seal 60 in the instrument seal assembly 40. The instrument seal 60 tightly abuts the instrument body, since the central aperture 61 is stretched due to dimensional difference between the aperture 61 and the instrument body. As the instrument is inserted further into the trocar 10, it encounters the passive valve seal 50 in the passive valve seal assembly 30 and separates the two planar valve members 54 as it passes through slit 55. Gases may now pass through the passive valve seal assembly 30, since the valve seal 50 does not seal against the instrument, but the gases are retained in the trocar 10 since they cannot now pass the combination of the instrument seal 60 and the instrument body. When the instrument is removed, the planar valve members 54 and slit 55 of the passive valve seal 50 close to block gas passage. Since the trocar apparatus 10 is a modular assembly, each of the main components 20, 30 and 40 may be discarded and replaced as needed. Optimally, the cannula 20 is made of a material able to be sterilized and reused, while the passive valve seal assembly 30 and the instrument seal assembly 40 are considered disposable, since sterilization of the seals 50 and 60 is impractical.

It is contemplated that certain equivalents and substitutions for components set forth above may be obvious to those skilled in the art, and the true scope and definition of the invention therefore is to be as set forth in the following claims.

I claim:

1. A trocar assembly which provides a conduit for gas and an instrument through the body wall of a patient and into an internal cavity, the trocar assembly having a distal end and a proximal end, comprising:

(A) a cannula comprising a tube and a mating member;

(B) a passive valve seal assembly comprising a cannula mating portion, an instrument seal assembly mating portion and a valve seal which is closed in the passive state to prevent passage of gas through said passive valve seal assembly and which opens to allow insertion of an instrument therethrough;

(C) an instrument assembly comprising a valve seal assembly mating portion and an instrument seal which prevents passage of gas through said instrument seal assembly in combination with an instrument inserted therethrough, said instrument seal assembly connected to said passive valve seal assembly;

where said cannula is releasably connected to said cannula mating portion of said combined passive valve seal assembly and instrument seal assembly to define a common axial bore extending from said distal end to said proximal end of said trocar assembly and said passive valve seal assembly is disposed intermediate said cannula and said instrument seal assembly;

where said mating portion of said cannula comprises cannula detent flanges and where said cannula mating portion of said passive valve seal assembly comprises pathway ribs defining an axial pathway for said cannula detent flanges which allows relative axial movement between said cannula and said passive valve seal assembly; and where said passive valve seal assembly further comprises axial detent flanges which abut said cannula detent flanges upon relative rotation of said cannula and said passive valve seal assembly, said axial detent flanges in combination with said cannula detent flanges preventing axial separation of said cannula and said passive valve seal assembly.

2. The trocar assembly of claim 1, where said passive valve seal assembly further comprises detent ribs and where said cannula detent flanges further comprise detent grooves, whereby said detent ribs interlock with said detent grooves upon relative rotation of said cannula and said passive valve seal assembly.

3. The trocar assembly of claim 2, where said valve seal comprises a pair of planar valve members and a slit at the junction of said planar valve members.

4. The trocar assembly of claim 3, where said instrument seal comprises a circular central aperture.

5. A trocar assembly which provides a conduit for gas and an instrument through the body wall of a patient and into an internal cavity, the trocar assembly having a distal end and a proximal end, comprising:

(A) a cannula comprising a tube and a mating member;

(B) a passive valve seal assembly comprising a cannula mating portion and a valve seal which is closed in the passive state to prevent passage of gas through said passive valve seal assembly and which opens to allow insertion of an instrument therethrough;

(C) an instrument seal assembly comprising an instrument seal which prevents passage of gas through said instrument seal assembly in combination with an instrument inserted therethrough, said instrument seal assembly connected to said passive valve seal assembly;

where said cannula is releasably connected to said cannula mating portion of said combined passive valve seal assembly and instrument seal assembly to define a common axial bore extending from said distal end to said proximal end of said trocar assembly and said passive valve seal assembly is disposed intermediate said cannula and said instrument seal assembly;

where said mating portion of said cannula comprises cannula detent flanges and where said cannula mating portion of said passive valve seal assembly comprises pathway ribs defining an axial pathway for said cannula detent flanges which allows relative axial movement between said cannula and said passive valve seal assembly; and where said passive valve seal assembly further comprises axial detent flanges which abut said cannula detent flanges upon relative rotation of said cannula and said passive valve seal assembly, said axial detent flanges in combination with said cannula detent flanges preventing axial separation of said cannula and said passive valve seal assembly.

6. The trocar assembly of claim 5, where said passive valve seal assembly further comprises detent ribs and where said cannula detent flanges further comprise detent grooves, whereby said detent ribs interlock with said detent grooves upon relative rotation of said cannula and said passive valve seal assembly.

7. The trocar assembly of claim 6, where said valve seal comprises a pair of planar valve members and a slit at the junction of said planar valve members.

8. The trocar assembly of claim 7, where said instrument seal comprises a circular central aperture.

9. A trocar assembly which provides a conduit for gas and an instrument through the body wall of a patient and into an internal cavity, the trocar assembly having a distal end and a proximal end, comprising:

(A) a cannula comprising a tube and a mating member;

(B) a passive valve seal assembly comprising a cannula mating portion, an instrument seal assembly mating portion and a valve seal which is closed in the passive state to prevent passage of gas through said passive valve seal assembly and which opens to allow insertion of an instrument therethrough;

(C) an instrument assembly comprising a valve seal assembly mating portion and an instrument seal which prevents passage of gas through said instrument seal assembly in combination with an instrument inserted therethrough, said instrument seal assembly connected to said passive valve seal assembly;

where said cannula is releasably connected to said cannula mating portion of said combined passive valve seal assembly and instrument seal assembly to define a common axial bore extending from said distal end to said proximal end of said trocar assembly and said passive valve seal assembly is disposed intermediate said cannula and said instrument seal assembly and where said passive valve seal assembly and said instrument seal assembly are permanently connected.

10. A trocar assembly which provides a conduit for gas and an instrument through the body wall of a patient and into an internal cavity, the trocar assembly having a distal end and a proximal end, comprising:

(A) a cannula comprising a tube and a mating member;

(B) a passive valve seal assembly comprising a cannula mating portion and a valve seal which is closed in the passive state to prevent passage of gas through said passive valve seal assembly and which opens to allow insertion of an instrument therethrough;

(C) an instrument seal assembly comprising an instrument seal which prevents passage of gas through said instrument seal assembly in combination with an instrument inserted therethrough, said instrument seal assembly connected to said passive valve seal assembly;

where said cannula is releasably connected to said cannula mating portion of said combined passive valve seal assembly and instrument seal assembly to define a common axial bore extending from said distal end to said proximal end of said trocar assembly and said passive valve seal assembly is disposed intermediate said cannula and said instrument seal assembly and where said passive valve seal assembly and said instrument seal assembly are permanently connected.

11. A trocar assembly which provides a conduit for gas and an instrument through the body wall of a patient and into an internal cavity, the trocar assembly having a distal end and a proximal end, comprising:

(A) a cannula comprising a tube and a mating member;

(B) a passive valve seal assembly comprising a cannula mating portion, an instrument seal assembly mating portion and a valve seal which is closed in the passive state to prevent passage of gas through said passive valve seal assembly and which opens to allow insertion of an instrument therethrough;

(C) an instrument seal assembly comprising a valve seal assembly mating portion and an instrument seal which prevents passage of gas through said instrument seal assembly in combination with an instrument inserted therethrough, said instrument seal assembly connected to said passive valve seal assembly;

where said cannula is releasably connected to said combined passive valve seal assembly and instrument seal assembly to define a common axial bore extending from said distal end to said proximal end of said trocar assembly and where said passive valve seal assembly and said instrument seal assembly are permanently connected.

12. A trocar assembly which provides a conduit for gas and an instrument through the body wall of a patient and into an internal cavity, the trocar assembly having a distal end and a proximal end, comprising:

(A) a cannula comprising a tube and a mating member joined by a transition shoulder whereby said mating member has a larger diameter than said tube, said mating member further comprising a pair of opposing cannula detent flanges extending circumferentially about said mating member;

(B) a passive valve seal assembly comprising a cannula mating portion which mates with said mating member of said cannula, an instrument seal assembly mating portion and a valve seal which is closed in the passive state to prevent passage of gas through said passive valve seal assembly and which opens to allow insertion of an instrument therethrough, said cannula mating portion further comprising an internal wall having opposing pairs of axially extending pathway ribs defining an axial pathway whereby said mating member of said cannula can be inserted in the axial direction into said cannula mating portion of said passive valve seal assembly, said cannula mating portion further comprising a pair of opposing axial detent flanges extending circumferentially about said internal wall, whereby said axial detent flanges about said cannula detent flanges after relative rotation of said cannula and said passive valve seal assembly after insertion of said mating member such that axial movement between said cannula and said passive valve seal assembly is prevented;

(C) an instrument seal assembly comprising a valve seal assembly mating portion which mates with said instrument seal assembly mating portion of said passive valve seal assembly and an instrument seal which prevents passage of gas through said instrument seal assembly in combination with an instrument inserted therethrough;

where said cannula, said passive valve seal assembly and said instrument seal assembly are connected to define a common axial bore extending from said distal end to said proximal end of said trocar assembly and where said passive valve seal assembly and said instrument seal assembly are permanently joined.

13. A trocar assembly which provides a conduit for gas and an instrument through the body wall of a patient and into an internal cavity, the trocar assembly having a distal end and a proximal end, comprising:

(A) a cannula comprising a tube and a mating member;

(B) a passive valve seal assembly comprising a cannula mating portion and a valve seal which is closed in the passive state to prevent passage of gas through said passive valve seal assembly and which opens to allow insertion of an instrument therethrough;

(C) an instrument seal assembly comprising an instrument seal which prevents passage of gas through said instrument seal assembly in combination with an instrument inserted therethrough, said instrument seal assembly connected to said passive valve seal assembly;

where said cannula is releasably connected to said combined passive valve seal assembly and instrument seal assembly to define a common axial bore extending from said distal end to said proximal end of said trocar assembly and where said passive valve seal assembly and said instrument seal assembly are permanently connected.

* * * * *